US00PP14312P29

(12) United States Plant Patent
Gilberg

(10) Patent No.: US PP14,312 P2
(45) Date of Patent: Nov. 25, 2003

(54) **ORNAMENTAL WINTER *HIBISCUS MOSCHEUTOS* NAMED 'MORRISON-GILBERG (X)'**

(50) Latin Name: *Hibiscus mosheutos*
Varietal Denomination: Morrison-Gilberg (X)

(76) Inventor: Douglas B. Gilberg, 2906 Ossenfort Rd., Glencoe, MO (US) 63038

( * ) Notice: Subject to any disclaimer, the term of this patent is extended or adjusted under 35 U.S.C. 154(b) by 0 days.

(21) Appl. No.: 09/528,911

(22) Filed: Mar. 20, 2000

(51) Int. Cl.[7] ..... A01H 5/00
(52) U.S. Cl. ..... Plt./257

(58) Field of Search ..... Plt./257

*Primary Examiner*—Bruce R. Campell
*Assistant Examiner*—Anne Marie Grünberg

(57) ABSTRACT

A new and distinct hybrid variety *Hibiscus moscheutos* cultivar, particularly distinguished by having flowers of from ten to twelve inches in diameter that are white with deep pink (Red-Purple Group 67A) venation concentrated at the outer margins of each petal, with deep pink eye (Red-Purple Group 67C). The length of the blooming cycle is about four to five weeks. The flowers, which have completely overlapping petals, retain their flat shape for two full days, except when temperatures are exceptionally warm. Distinguishing characteristics are constant and stable in asexually reproduced plants.

1 Drawing Sheet

BACKGROUND OF THE INVENTION

The present invention relates to a new and distinct variety of herbaceous perennial, more particularly to a variety of hibiscus.

BRIEF SUMMARY OF THE INVENTION

The new cultivar was found by Douglas B. Gilberg in the cultivated outdoor breeding area of Gilberg Perennial Farms, Inc., in Wildwood, Mo., a suburb of St. Louis, Mo. The new cultivar is evidently the result of natural cross-pollination. It was found on one branch of a red seedling (unnamed and unpatented) in a cultivated area. Its parentage cannot be identified. The plant is a hybrid of unnamed and unpatented parentage. I have asexually reproduced the plant by root crown division in a greenhouse located at the nursery of Gilberg Perennial Farms, 3209 Bouquet Road, Pacific, Mo. 63069. The plant has also been reproduced by vegetative reproduction, i.e., by tip and stem cuttings. The present cultivar is a herbaceous perennial; the stalks die back to ground level every winter and new stalks emerge in late spring. The trade name "PITTER PATTI" has been coined for this cultivar, although the cultivar was neither marketed nor was its existence made public prior to the filing of the present plant patent application.

The present cultivar is distinguished by having flowers of from ten to twelve inches in diameter. These unusually large flowers can be cut and used for centerpiece displays. By comparison, *Hibiscus rosa-sinensis* (Chinese Hibiscus Rose of China) flowers are two to six inches in diameter, and *Hibiscus syriacus* (Rose-of-Sharon or Althea) flowers are three to six inches in diameter.

The greatest number of flowers for the present cultivar was obtained in environments of half to full sun. The largest flowers were obtained at summer temperatures from 70 to 100 degrees Fahrenheit. Smaller flowers were observed to bloom at temperatures as low as 50 to 60 degrees Fahrenheit.

Reproduction by root crown division consistently produces plants with identical, stable characteristics. A further botanical description of the new variety follows below. In the following descriptions, color references are made to The R.H.S. Colour Chart (1995, The Royal Horticultural Society), except where general terms of ordinary significance are used. Distinguishing color characteristics are listed on the attached Plant Color Coding Sheet. The distinguishing characteristics listed thereon should not necessarily be assumed to be exhaustive. Although the listed characteristics are believed to be the primary distinguishing color characteristics of the cultivar, it is possible that others may become evident upon further observation and comparison with other cultivars. These descriptions were made from specimens reproduced and grown under greenhouse and outdoor gardening conditions in suburban St. Louis, Mo.

BRIEF DESCRIPTION OF THE DRAWINGS

The accompanying drawing clearly depicts the new variety, showing the colors as true as it is reasonably possible to obtain in a colored reproduction of this type. Actual flower, leaf, sepal, and bud colors may differ from flower, leaf, sepal, and bud colors in the photograph due to light reflectance.

The drawing is a close-up view of freshly cut portions of the *Hibiscus moscheutos* named 'Morrison-Gilberg (X)' cultivar of the present invention, showing the flower, leaves and sepal surrounding the flower bud in great detail.

DETAILED BOTANICAL DESCRIPTION

Figure 1:
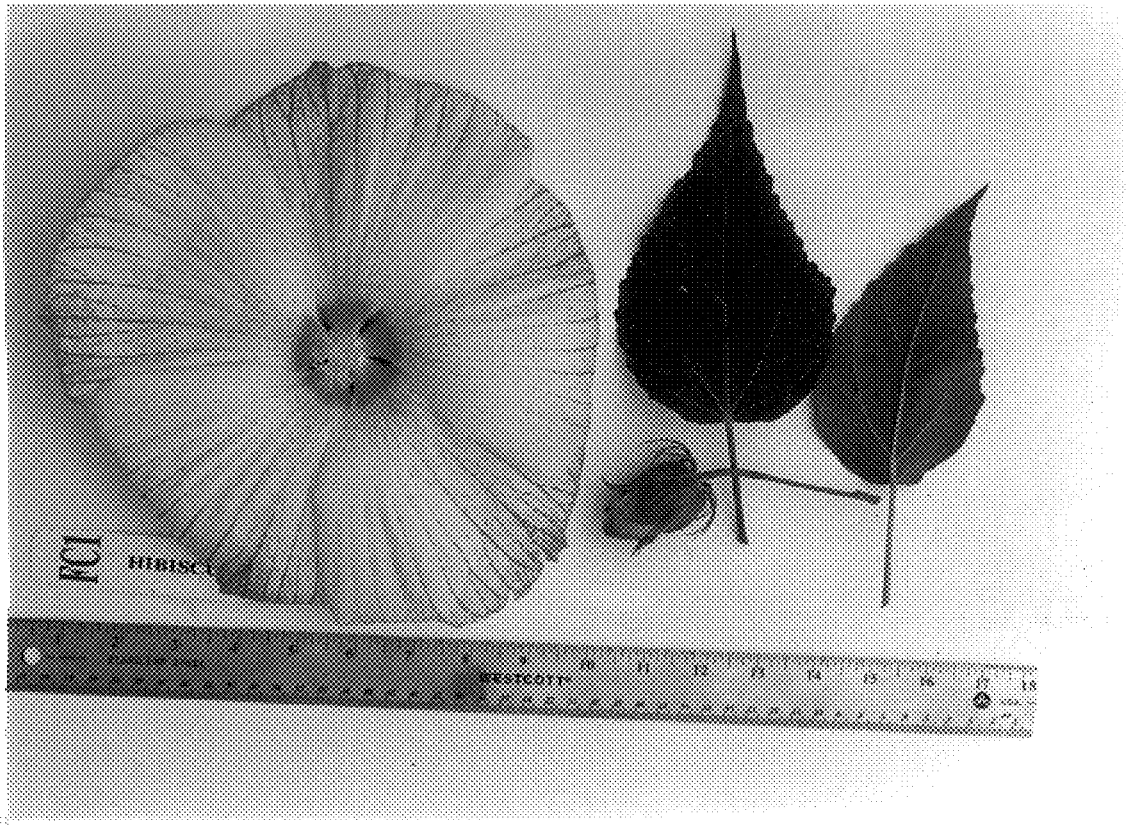

Form: Numerous stalks grow upright from perennial roots.

Habit: Individual stalks with many leaves uniformly distributed on the stalk and numerous flowers bloom continuously. Rapid and strong stalk growth have flowers facing outward.

Productivity: Produces continuous new flower displays, vigorous and profuse.

Precocity: Elegant displays of flowers, each stalk displaying one new flower after another. On each stalk, as one flower closes and its petals fall off, a flower next to it and closer to the top of the stalk blooms, so that the displays appear to be continuous. The display periods may vary depending upon climate and the vigor of particular specimens.

Stalks: Mature presentations occur the first year. Strong and smooth skin covered, and hold many leaves and flowers securely. Staking is typically not required under normal full sun growing conditions. However, specimens grown in shaded sunlight produce stalks that are softer and that may require staking. New stalks emerge in May.

Temperature: Winter hardy during freezing winters. On 100 degree (Fahrenheit) days, the flowers bloom equally as they do on a mild day.

Insects: Negligible insect damage has occurred to date in any individual plant, even though no pesticides have been used, and no slugs have been observed on the plants.

Animals: Rodents, rabbits and squirrels have not been observed to bother the stalks or roots.

Rooting: The plants root easily without fertilizer and send out their roots quickly and securely.

Foliage: Large leaves evenly distributed vertically and horizontally on the stalks.

Stems: Green Group 136C.

Leaves: Abundant and decorative in alternate order. Medium to dark green leaves with margin lengths of from three to seven inches in elongated heart form. Typical leaves are seven inches long by about three to four inches wide at the widest part. Top color is Green Group 132B, bottom color is Green Group 136B. Shape is generally cordate, with somewhat irregular crenate margins. Leaf tips are apiculate, bases are cordate, and the venation is pinnate. Texture is matte. Petioles are from two to four and one-half inches. No stipules.

Petiole color: Lighter green (Green Group 138C) than the leaves, tending toward red (Greyed-Red Group 178B) at maturity.

Height: Mature plants are from three to five and one-half feet in height.

Shape of plant at maturity: Rounded, almost globe-shaped.

THE FLOWERS

Buds: Shaped like a pointed egg and very large one to two days before blooming. Red Group 36C with tips colored Red Group 51B. Very large, can be up to five inches in length. A typical bud measures about three inches in length by about one and one-quarter inches at its widest point.

Blooming habit: Continuous and free blooming.

Petals: Five to six inches long, five and one-half inches wide, five per flower.

Diameter of flower: A distinguishing feature of the variety, flowers are from ten to twelve inches in diameter.

Number of flowers: Approximately 12 to 15 flowers per stalk in mature plants, with essentially flat appearance.

Shape: Circular and relatively flat with overlapping petals.

Filament: Each of the approximately 15 filaments attaches to the large style projecting from the center of the flower. Approximately one-eighth to one-quarter inches in length.

Stamens: Three-eighths of an inch long, Yellow Group 4D, very numerous, extending from the style.

Pistil: Three and one-eighths of an inch long with the stamen and stigma attached. White Group 155D.

Stigma: Five, Yellow Group 4D.

Style: Yellow. Long and supports the stigma.

Pollen: Yellow Group 5D.

Shape of petal: Overlapping and broadly obovate (almost reniform), recurves at the base to form a small green star of revealed calyx, with overall circular shape.

Texture: Central one-fourth satiny; outer three-fourths velvety.

Aspect: Like fine kidskin in appearance and strongly self-supporting.

Color: White with deep pink (Red-Purple Group 67A) venation concentrated at the outer margins of each petal, with deep pink eye (Red-Purple Group 67C). The eye is two inches wide. Constant and stable in asexually reproduced plants.

Calyx: Six sepals, one and one-half inches long and one and one-quarter inches wide, Green Group 136B Bractlets: Twelve bractlets, one and one-half inches long and three-sixteenths inch wide at the base, medium green (Green Group 132C).

Blooming period: Mid summer to frost with continuous color presentation. In suburban St. Louis, the blooming period typically lasts from late July through August. Blooms can occur into October, depending on weather conditions. Container plants produce flowers longer, on lateral stems, as the main stems are cut back and laterals emerge.

Lastingness of the bloom: Individual blooms allowed to remain on the plant last approximately one to three days per bloom.

Peduncle: One and one-half to three inch extremely stiff pedicels, Green Group 132C, to support the flower during blooming and the seed pod formation later.

Fruit: Twelve to eighteen seeds produced; fruit one inch long and three-quarters inch wide.

Fragrance: Minimal.

Disease resistance: No disease problems have been noted on stalks, leaves or flowers.

Environmental conditions: The plants can stand drought or up to two inches of rainwater without adverse effects.

Winter dormancy: The plants lose their leaves at frost and stems die back to ground level.

Fertility: Midwest topsoil provides adequate nutrients without additional fertilizer.

Regularity of bearing: Consistent year-to-year flowering has been observed.

I claim:

1. A new and distinct variety of *Hibiscus moscheutos* plant, as herein shown and described.

* * * * *